United States Patent
Kawashima

(10) Patent No.: US 11,460,206 B2
(45) Date of Patent: Oct. 4, 2022

(54) REFRIGERANT DETECTION APPARATUS

(71) Applicant: Mitsubishi Electric Corporation, Tokyo (JP)

(72) Inventor: Mitsuru Kawashima, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 503 days.

(21) Appl. No.: 16/468,316

(22) PCT Filed: Mar. 10, 2017

(86) PCT No.: PCT/JP2017/009755
§ 371 (c)(1),
(2) Date: Jun. 11, 2019

(87) PCT Pub. No.: WO2018/163417
PCT Pub. Date: Sep. 13, 2018

(65) Prior Publication Data
US 2019/0383508 A1    Dec. 19, 2019

(51) Int. Cl.
*F24F 11/36*    (2018.01)
*G01N 33/00*    (2006.01)

(52) U.S. Cl.
CPC .......... *F24F 11/36* (2018.01); *G01N 33/0022* (2013.01)

(58) Field of Classification Search
CPC ............................. G01N 33/0022; F24F 11/36
See application file for complete search history.

(56) References Cited

U.S. PATENT DOCUMENTS

| | | | |
|---|---|---|---|
| 2013/0098576 A1 | 4/2013 | Fujitaka et al. | |
| 2014/0196483 A1* | 7/2014 | Okazaki | F25B 25/005 62/126 |
| 2015/0028209 A1* | 1/2015 | Harju | G01M 3/222 250/338.5 |
| 2019/0242632 A1* | 8/2019 | Sakae | F25B 49/005 |
| 2019/0390877 A1* | 12/2019 | Sakae | F25B 1/00 |

(Continued)

FOREIGN PATENT DOCUMENTS

| | | |
|---|---|---|
| JP | H03-027576 U | 3/1991 |
| JP | 2005-016822 A | 1/2005 |

(Continued)

OTHER PUBLICATIONS

International Search Report of the International Searching Authority dated May 30, 2017 for the corresponding International application No. PCT/JP2017/009755 (and English translation).

(Continued)

*Primary Examiner* — Peter J Macchiarolo
*Assistant Examiner* — Fatemeh Esfandiari Nia
(74) *Attorney, Agent, or Firm* — Posz Law Group, PLC

(57) ABSTRACT

A refrigerant detection apparatus that is able to detect refrigerant having leaked in a plurality of rooms using sensors the number of which is smaller than the number of rooms serving as detection targets includes a sensor configured to be able to detect refrigerant being filled in a refrigerant pipe of an air conditioner, and a casing that houses the sensor. The casing has a first opening configured to be able to connect to the inside of a room, and a second opening configured to be able to connect to the inside of a room different from the room being able to be connected to the first opening.

7 Claims, 5 Drawing Sheets

(56) References Cited

U.S. PATENT DOCUMENTS

2020/0166470 A1* 5/2020 Chen .................. G01N 27/16
2021/0108819 A1* 4/2021 Chen .................. F24F 11/36

FOREIGN PATENT DOCUMENTS

| JP | 2009-258950 A | | 11/2009 |
|----|---------------|---|---------|
| JP | 2009258950 A | * | 11/2009 |
| JP | 2010-092135 A | | 4/2010 |
| JP | 2012-013348 A | | 1/2012 |
| JP | 2014-081160 A | | 5/2014 |
| KR | 20110008888 U | | 9/2011 |

OTHER PUBLICATIONS

Office Action dated Oct. 6, 2020 in the corresponding JP patent application No. 2019-504278 (and English translation).
Office Action dated Aug. 3, 2021 in the corresponding JP patent application No. 2019-504278 (and English translation).
Extended European Search Report dated Jan. 28, 2020 issued in corresponding EP patent application No. 17900267.0.
Office Action dated Feb. 16, 2022 issued in corresponding EP Patent Application No. 17900267.0.

* cited by examiner

REFRIGERANT DETECTION APPARATUS

CROSS REFERENCE TO RELATED APPLICATION

This application is a U.S. national stage application of PCT/JP2017/009755 filed on Mar. 10, 2017, the contents of which are incorporated herein by reference.

TECHNICAL FIELD

The invention relates to a refrigerant detection apparatus.

BACKGROUND ART

A technique in which refrigerant leakage detection means for detecting refrigerant leakage is provided in an air conditioner, and an alarm is issued when the refrigerant leakage detection means detects the refrigerant leakage has been known (see, e.g., PTL 1).

CITATION LIST

Patent Literature

[PTL 1] Japanese Patent Application Publication No. 2012-013348

SUMMARY OF INVENTION

Technical Problem

However, in the technique disclosed in PTL 1, the refrigerant leakage detection means for detecting the refrigerant leakage, i.e., a sensor is provided for each air conditioner. Accordingly, for example, in what is called a multiple type in which a plurality of indoor units are connected to one outdoor unit, sensors equal in number to the indoor units are necessary. That is, in the case where the indoor unit of the air conditioner is installed in each of a plurality of rooms, in order to detect refrigerant having leaked in the plurality of rooms, sensors equal in number to the rooms serving as detection targets are necessary.

The invention has been made in order to solve the above problem. An object thereof is to obtain a refrigerant detection apparatus that is able to detect refrigerant having leaked in a plurality of rooms using sensors the number of which is smaller than the number of rooms serving as detection targets.

Solution to Problem

A refrigerant detection apparatus according to the present invention includes: a sensor configured to be able to detect refrigerant being filled in a refrigerant pipe of an air conditioner, and a casing configured to house the sensor, the casing having: a first opening configured to be able to connect to inside of a room, and a second opening configured to be able to connect to inside of a room different from the room being able to be connected to the first opening.

Advantageous Effects of Invention

The refrigerant detection apparatus according to the invention exhibits an effect of being able to detect the refrigerant having leaked in the plurality of rooms using the sensors the number of which is smaller than the number of the rooms serving as the detection targets.

DESCRIPTION OF EMBODIMENTS

Figure 1:
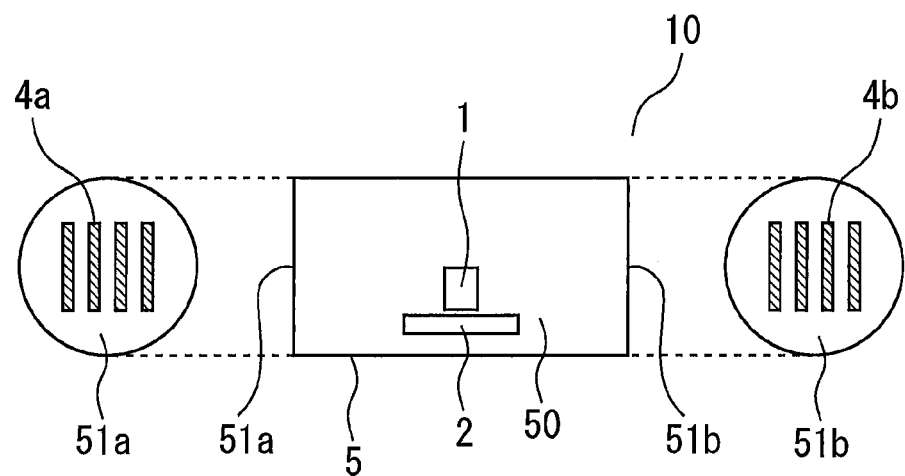
FIG. 1 is a view schematically showing the configuration of a refrigerant detection apparatus according to Embodiment 1 of the present invention.

Embodiments of the invention will be described with reference to the accompanying drawings. In the drawings, the same or corresponding parts are designated by the same reference numerals, and the repeated description thereof will be appropriately simplified or omitted. Note that the present invention is not limited to the following embodiments, and can be variously modified without departing from the gist of the present invention.

Embodiment 1

Figure 2:
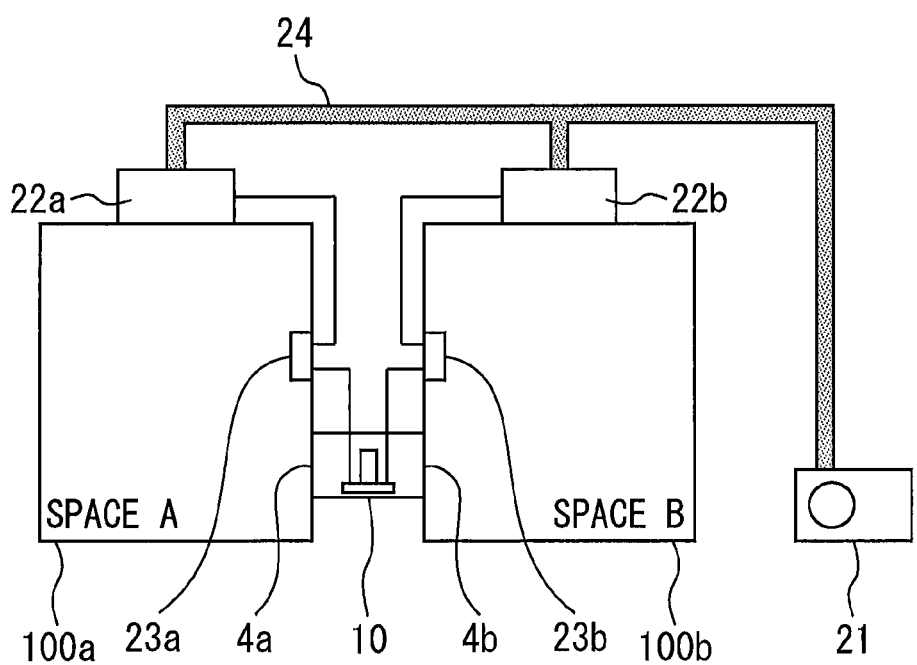
FIG. 2 is a view schematically showing an example of the installation of the refrigerant detection apparatus according to Embodiment 1 of the present invention.

FIG. 1 and FIG. 2 are associated with Embodiment 1 of the invention, FIG. 1 is a view schematically showing the configuration of a refrigerant detection apparatus, and FIG. 2 is a view schematically showing an example of the installation of the refrigerant detection apparatus.

As shown in FIG. 1, a refrigerant detection apparatus 10 according to Embodiment 1 of the invention includes a sensor 1, a leakage determination portion 2, and a casing 5. Note that the center of FIG. 1 is a front view of the refrigerant detection apparatus 10 in a see-through state that shows the inside thereof. One of the left and the right of FIG. 1 is a side view of one end side of the refrigerant detection apparatus 10. The other one of the left and the right of FIG. 1 is a side view of the other end side of the refrigerant detection apparatus 10.

The sensor 1 is able to detect refrigerant. As the sensor 1, various types of sensors such as, e.g., a contact combustion sensor, a semiconductor sensor, a heat conduction sensor, a controlled potential electrolysis sensor, and an infrared sensor may be adopted. In addition, an oxygen sensor may also be used as the sensor 1. The oxygen sensor is the sensor that detects an oxygen concentration in the air. As the oxygen sensor used as the sensor 1, various types of sensors such as, e.g., a galvanic cell sensor, a polarographic sensor, and a zirconia sensor may be used.

In the case where the oxygen sensor is used as the sensor 1, the concentration of refrigerant may be detected, for example, in the following manner. That is, first, the oxygen concentration is determined based on an output from the oxygen sensor. Next, assuming that a reduction in oxygen concentration is caused by inflow gas, the concentration of the inflow gas is determined. Subsequently, by assuming that the inflow gas is the refrigerant, the concentration of the inflow gas, i.e., the refrigerant can be obtained.

The sensor 1 outputs a detection signal in accordance with the detected refrigerant concentration. The leakage determination portion 2 determines whether or not refrigerant leakage has occurred in the internal space of a room serving as a detection target of the refrigerant detection apparatus 10 based on the detection signal outputted from the sensor 1. Specifically, in the case where the sensor 1 detects the refrigerant concentration that is equal to or higher than a preset reference concentration, the leakage determination portion 2 determines that the refrigerant leakage is detected by the sensor 1. Note that the detection of the refrigerant concentration of equal to or higher than the reference concentration by the sensor 1 is also referred to as "the sensor 1 has detected the refrigerant leakage".

The casing 5 is the exterior of the refrigerant detection apparatus 10. The casing 5 has, e.g., a hollow bottomed cylindrical shape. The sensor 1 is housed in the casing 5. That is, the sensor 1 is disposed in a sensor disposition portion 50 in the casing 5. In addition, the leakage determination portion 2 is also housed in the sensor disposition portion 50 in the casing 5.

Two cylindrical bottom surfaces of the casing 5 are opening formation surfaces. That is, one of the cylindrical bottom surfaces of the casing 5 is a first opening formation surface 51a. The other one of the cylindrical bottom surfaces of the casing 5 is a second opening formation surface 51b. Each of the first opening formation surface 51a and the second opening formation surface 51b is a flat surface. In Embodiment 1, the first opening formation surface 51a and the second opening formation surface 51b are parallel to each other.

A first opening 4a is formed in the first opening formation surface 51a. A second opening 4b is formed in the second opening formation surface 51b. The first opening 4a is constituted by, e.g., a plurality of slit-shaped openings. Similarly, the second opening 4b is also constituted by, e.g., a plurality of slit-shaped openings.

The first opening 4a passes through the inside and the outside of the casing 5. Accordingly, the sensor disposition portion 50 in the casing 5 communicates with the outside of the casing 5 via the first opening 4a. Similarly, the second opening 4b also passes through the inside and the outside of the casing 5. Accordingly, the sensor disposition portion 50 in the casing 5 communicates with the outside of the casing 5 also via the second opening 4b.

Next, a description will be given of an example in which the thus configured refrigerant detection apparatus 10 is installed such that the refrigerant detection apparatus 10 is usable with reference to FIG. 2. In an environment in which the refrigerant detection apparatus 10 according to Embodiment 1 of the invention is installed, a plurality of rooms are present. Herein, as shown in FIG. 2, an example in which a first room 100a and a second room 100b are present as the plurality of rooms will be described.

An air conditioner is installed for the first room 100a and the second room 100b. The air conditioner includes indoor units, an outdoor unit 21, and remote controllers. The indoor unit is installed in a target room to be air-conditioned. That is, a first indoor unit 22a is installed in the first room 100a. In addition, a second indoor unit 22b is installed in the second room 100b.

The first indoor unit 22a is able to suck in indoor air in the first room 100a. In addition, the first indoor unit 22a is able to blow adjusted air into the first room 100a. Similarly, the second indoor unit 22b is able to suck in indoor air in the second room 100b. In addition, the second indoor unit 22b is able to blow adjusted air into the second room 100b.

The outdoor unit 21 is installed outside the first room 100a and the second room 100b. The first indoor unit 22a, the second indoor unit 22b, and the outdoor unit 21 are connected to each other via a refrigerant pipe 24. Refrigerant is filled in the refrigerant pipe 24. The refrigerant pipe 24 is provided to circulate through the first indoor unit 22a, the second indoor unit 22b, and the outdoor unit 21. Thus, the air conditioner is what is called a multiple type in which a plurality of the indoor units (the first indoor unit 22a and the second indoor unit 22b) are connected to one outdoor unit 21.

It is preferable to use refrigerant having a low global warming potential (GWP) as the refrigerant filled in the refrigerant pipe 24 from the viewpoint of global environmental protection. The refrigerant filled in the refrigerant pipe 24 is combustible. This refrigerant has an average molecular weight higher than that of air (i.e., has a density higher than that of air), and has a property that the refrigerant sinks downward in the direction of gravity in the air.

Specific examples of the refrigerant which may be used include a refrigerant consisting of one or more refrigerants (mixture) selected from tetrafluoropropene ($CF_3CF=CH_2$: HFO-1234yf), difluoromethane ($CH_2F_2$:R32), propane (R290), propylene (R1270), ethane (R170), butane (R600), isobutane (R600a), 1,1,1,2-tetrafluoroethane ($C_2H_2F_4$: R134a), pentafluoroethane ($C_2HF_5$:R125), and 1,3,3,3-tetrafluoro-1-propene ($CF_3$-$CH=CHF$:HFO-1234ze).

The remote controller of the air conditioner is used by a user for operating the operation of the air conditioner. In an example shown in FIG. 2, a first remote controller 23a is installed on a wall surface portion of the first room 100a. In addition, the first indoor unit 22a is installed on a ceiling portion of the first room 100a. Accordingly, the first remote controller 23a is disposed vertically below the first indoor unit 22a. The first remote controller 23a is electrically connected to the first indoor unit 22a. The user can start and stop the operation of the first indoor unit 22a and change set temperature by operating the first remote controller 23a.

Similarly, in the example shown in the drawing, a second remote controller 23b is installed on a wall surface portion of the second room 100b. In addition, the second indoor unit 22b is installed on a ceiling portion of the second room 100b. Accordingly, the second remote controller 23b is disposed vertically below the second indoor unit 22b. The second remote controller 23b is electrically connected to the second indoor unit 22b. The user can start and stop the operation of the second indoor unit 22b and change set temperature by operating the second remote controller 23b.

The first room 100a and the second room 100b are, e.g., adjacent to each other. An indoor space A of the first room 100a and an indoor space B of the second room 100b are separated from each other by a wall. The refrigerant detection apparatus 10 is to be disposed between a wall surface of the first room 100a and a wall surface of the second room 100b. Note that the wall surface of the first room 100a on the side of the second room 100b and the wall surface of the second room 100b on the side of the first room 100a are parallel to each other.

The first opening formation surface 51a of the refrigerant detection apparatus 10 is exposed to the indoor space A of the first room 100a. Accordingly, the first opening 4a of the refrigerant detection apparatus 10 connects to the indoor space A of the first room 100a. In addition, the second opening formation surface 51b of the refrigerant detection apparatus 10 is exposed to the indoor space B of the second room 100b. Accordingly, the second opening 4b of the refrigerant detection apparatus 10 connects to the indoor space B of the second room 100b.

Thus, the first opening 4a is able to connect to the inside of the first room 100a serving as the room. The second opening 4b is able to connect to the inside of the second room 100b serving as the room. The first room 100a and the second room 100b are different rooms. Accordingly, the second opening 4b is able to connect to the inside of the room (the second room 100b in the example in FIG. 2) that is different from the room (the first room 100a in the example in FIG. 2) that is able to be connected to the first opening 4a.

Accordingly, the air in the indoor space A of the first room 100a can enter the casing 5 through the first opening 4a, and reach the sensor disposition portion 50. In addition, the air in the indoor space B of the second room 100b can enter the casing 5 through the second opening 4b, and reach the sensor disposition portion 50.

As the sensor 1 of the refrigerant detection apparatus 10, a sensor that is able to detect the refrigerant filled in the refrigerant pipe 24 of the air conditioner is used. The leakage determination portion 2 of the refrigerant detection apparatus 10 is electrically connected to each of the first remote controller 23a and the second remote controller 23b. In the case where the sensor 1 detects the refrigerant leakage, the leakage determination portion 2 outputs a leakage detection signal to each of the first remote controller 23a and the second remote controller 23b.

Each of the first remote controller 23a and the second remote controller 23b provides notification upon receiving the leakage detection signal from the leakage determination portion 2 to notify the user or the like that the refrigerant leakage is detected. The provision of the notification is performed specifically by, e.g., emitting a sound from a speaker. In this case, each of the first remote controller 23a and the second remote controller 23b includes a speaker for emitting a sound that is not shown. As the sound emitted from the speaker in the provision of the notification, it is conceivable to use, e.g., a beep, a voice message, or a combination thereof.

In addition, at this point, at the same time as the sound is emitted from the speaker, a lamp may be turned on. In this case, each of the first remote controller 23a and the second remote controller 23b includes a lamp for emitting light that is not shown. As the lamp, it is conceivable to use, e.g., an LED (light-emitting diode).

Note that the leakage determination portion 2 may be electrically connected to each of the first indoor unit 22a and the second indoor unit 22b. The above-described provision of the notification that uses sound or light may be performed in each of the first indoor unit 22a and the second indoor unit 22b. In addition, a circuit shut-off valve such as an electromagnetic valve may be provided at some midpoint of the refrigerant pipe 24, and the circuit shut-off valve may be closed in the case where each of the first indoor unit 22a and the second indoor unit 22b receives the leakage detection signal from the leakage determination portion 2. With this, the leakage amount of the refrigerant can be minimized.

The installation position of the refrigerant detection apparatus 10 is adjusted such that the first opening 4a is disposed vertically below the first remote controller 23a, and the second opening 4b is disposed vertically below the second remote controller 23b.

In the case where, as described above, the refrigerant is heavier than air, the refrigerant that has leaked flows vertically downward from the first indoor unit 22a or the second indoor unit 22b. Accordingly, the refrigerant that has leaked tends to accumulate on a lower side of the first room 100a or the second room 100b, and form a high-concentration area. To cope with this, by providing the refrigerant detection apparatus 10 including the sensor 1 at a position on the lower sides of the first room 100a and the second room 100b, e.g., vertically below the first remote controller 23a and the second remote controller 23b that are usually installed at positions that facilitate the operation by the user, the detection of the refrigerant that has leaked by the sensor 1 can be facilitated. Note that the installation position of the refrigerant detection apparatus 10 is preferably installed at a position apart from a floor surface of each of the first room 100a and the second room 100b at a distance of about 50 cm or less.

Next, a description will be given of an example of the operation of the refrigerant detection apparatus 10 in the case where the refrigerant detection apparatus 10 having the above-described configuration is installed in the manner described above. In the case where the refrigerant has leaked from the refrigerant pipe 24 due to, e.g., breakage caused by vibrations or corrosion, when the leakage location of the refrigerant is in a cabinet of the first indoor unit 22a, the refrigerant in the refrigerant pipe 24 is released into the cabinet of the first indoor unit 22a first. Subsequently, the refrigerant that has leaked leaks into the indoor space A of the first room 100a through an opening such as an inlet or an outlet of the first indoor unit 22a.

As described above, the first opening 4a of the refrigerant detection apparatus 10 connects to the indoor space A of the first room 100a. The refrigerant having leaked into the indoor space A of the first room 100a enters the casing 5 through the first opening 4a. At this point, as described above, the refrigerant is heavier than air, and hence the refrigerant that has leaked falls vertically downward, and accumulates on the floor surface of the first room 100a. Subsequently, when the upper end of the area where the refrigerant has accumulated on the floor surface of the first room 100a reaches the position of the first opening 4a, the refrigerant enters the casing 5 from the first opening 4a.

The refrigerant having entered the casing 5 from the first opening 4a reaches the sensor disposition portion 50, and comes into contact with the sensor 1. Subsequently, when the refrigerant concentration of the sensor disposition portion 50 becomes equal to or more than the reference value described above, the leakage determination portion 2 outputs the leakage detection signal.

Meanwhile, in the case where the leakage location of the refrigerant is in a cabinet of the second indoor unit 22b, the refrigerant in the refrigerant pipe 24 is released into the cabinet of the second indoor unit 22b. Subsequently, the refrigerant that has leaked leaks into the indoor space B of the second room 100b through an opening such as an inlet or an outlet of the second indoor unit 22b.

As described above, the second opening 4b of the refrigerant detection apparatus 10 connects to the indoor space B of the second room 100b. The refrigerant having leaked into the indoor space B of the second room 100b enters the casing 5 through the second opening 4b. At this point, as described above, the refrigerant is heavier than air, and hence the refrigerant that has leaked falls vertically downward, and accumulates on the floor surface of the second room 100b. Subsequently, when the upper end of the refrigerant having accumulated on the floor surface of the second room 100b reaches the position of the second opening 4b, the refrigerant enters the casing 5 from the second opening 4b.

The refrigerant having entered the casing 5 from the second opening 4b reaches the sensor disposition portion 50, and comes into contact with the sensor 1. Subsequently, when the refrigerant concentration of the sensor disposition portion 50 becomes equal to or more than the reference value described above, the leakage determination portion 2 outputs the leakage detection signal.

Thus, the refrigerant detection apparatus 10 is able to detect both of the refrigerant having leaked into the indoor space A of the first room 100a and the refrigerant having leaked into the indoor space B of the second room 100b using one sensor 1 to output the leakage detection signal. Accordingly, the refrigerant detection apparatus 10 according to Embodiment 1 of the invention is able to detect the refrigerant having leaked in a plurality of different rooms using sensors the number of which is smaller than the number of rooms serving as detection targets. Accordingly, even when the number of rooms serving as detection targets is increased, the number of necessary sensors can be reduced, and the refrigerant detection apparatus 10 that has a plurality of rooms as detection targets at low cost can be implemented.

Further, as described above, each of the first opening formation surface 51a in which the first opening 4a is formed and the second opening formation surface 51b in which the second opening 4b is formed is a flat surface. Accordingly, the casing 5 does not protrude from the wall surface when the refrigerant detection apparatus 10 is installed, and the casing 5 does not interfere with anything or spoil beauty.

Note that a filter for removing a foreign object such as dust from passing air may be provided in each of the first opening 4a and the second opening 4b. With this configuration, contamination of the foreign object such as dust into the casing 5 can be prevented. Accordingly, a malfunction of the sensor 1 due to attachment of the foreign object such as dust to the sensor 1 can be prevented.

In addition, the place where the leakage determination portion 2 is housed is not limited to the casing 5 of the refrigerant detection apparatus 10. In addition to the casing 5, for example, the leakage determination portion 2 may also be provided in each of the first remote controller 23a and the second remote controller 23b. Further, in addition to them, for example, the leakage determination portion 2 may also be provided in each of the first indoor unit 22a and the second indoor unit 22b.

Embodiment 2

Figure 3:
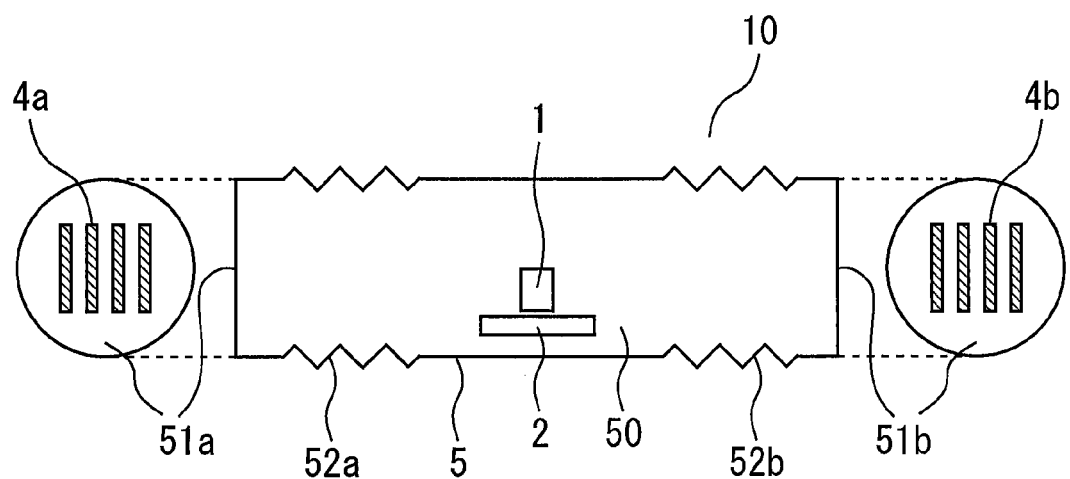
FIG. 3 is a view schematically showing the configuration of the refrigerant detection apparatus according to Embodiment 2 of the present invention.

FIG. 3 is associated with Embodiment 2 of the invention, and is a view schematically showing the configuration of the refrigerant detection apparatus.

In Embodiment 2 described herein, in addition to the configuration of Embodiment 1 described above, a changeable portion that is able to change one or both of relative positions and relative directions of the first opening formation surface and the second opening formation surface is provided in the casing of the refrigerant detection apparatus. Hereinafter, by using the case based on the configuration of Embodiment 1 as an example, a description will be given of the refrigerant detection apparatus according to Embodiment 2 with a focus on points different from Embodiment 1.

As shown in FIG. 3, a first changeable portion 52a and a second changeable portion 52b are provided in the casing 5 of the refrigerant detection apparatus 10 according to Embodiment 2 of the invention. The first changeable portion 52a is provided between the sensor disposition portion 50 and the first opening formation surface 51a in the casing 5. The second changeable portion 52b is provided between the sensor disposition portion 50 and the second opening formation surface 51b in the casing 5.

Each of the first changeable portion 52a and the second changeable portion 52b is formed by using at least either one of a freely bendable structure and a freely bendable material. Examples of the freely bendable structure include a bellows and the like. Examples of the freely bendable material include soft vinyl resin and silicon resin. FIG. 3 shows an example in which each of the first changeable portion 52a and the second changeable portion 52b is constituted by the bellows.

One or both of the position and the direction of the first opening formation surface 51a with respect to the sensor disposition portion 50 can be changed by bending the first changeable portion 52a to deform the external shape of the casing 5. In addition, one or both of the position and the direction of the second opening formation surface 51b with respect to the sensor disposition portion 50 can be changed by bending the second changeable portion 52b to deform the external shape of the casing 5.

Accordingly, one or both of the relative positions and the relative directions of the first opening formation surface 51a and the second opening formation surface 51b can be changed with the first changeable portion 52a and the second changeable portion 52b.

Other configurations are the same as those in Embodiment 1, and the description thereof will be omitted.

Also in the thus configured refrigerant detection apparatus 10, the effects similar to those of Embodiment 1 can be exhibited. Further, the relative directions of the first opening formation surface 51a and the second opening formation surface 51b can be changed by using the first changeable portion 52a and the second changeable portion 52b in accordance with the direction of the wall surface of each of the first room 100a and the second room 100b for which the refrigerant detection apparatus 10 is installed. Accordingly, even in the case where the wall surface of the first room 100a and the wall surface of the second room 100b are not parallel to each other, it is possible to dispose the first opening formation surface 51a parallel to the wall surface of the first room 100a, and dispose the second opening formation surface 51b parallel to the wall surface of the second room 100b.

In addition, it is possible to freely set each of the position of the first opening 4a in the first room 100a and the position of the second opening 4b in the second room 100b within a specific area. Further, it is also possible to change a distance between the first opening formation surface 51a and the second opening formation surface 51b in accordance with a distance between the wall surface of the first room 100a and the wall surface of the second room 100b. Thus, it is possible to flexibly and properly cope with various positional relationships of a plurality of rooms for which the refrigerant detection apparatus 10 is to be installed by deforming the casing 5.

According to the refrigerant detection apparatus 10 of Embodiment 2, the first opening 4a may be disposed not on the wall surface of the first room 100a but on the floor surface thereof. In addition, similarly, the second opening 4b may be disposed not on the wall surface of the second room 100b but on the floor surface thereof. As described above, the refrigerant that is heavier than air accumulates on the floor surface of the first room 100a or the second room 100b. To cope with this, by disposing each of the first opening 4a and the second opening 4b on the floor surface, the refrigerant leakage can be detected in a shorter period of time.

Note that both of the first changeable portion 52a and the second changeable portion 52b need not necessarily be provided. That is, it is only required that at least one of the first changeable portion 52a and the second changeable portion 52b is provided.

Embodiment 3

Figure 4:
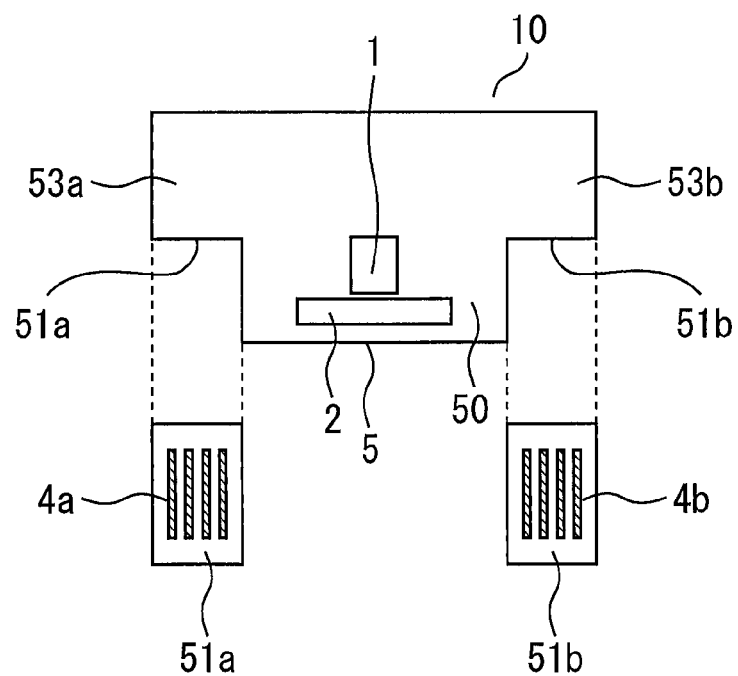
FIG. 4 is a view schematically showing the configuration of the refrigerant detection apparatus according to Embodiment 3 of the present invention.
Figure 5:
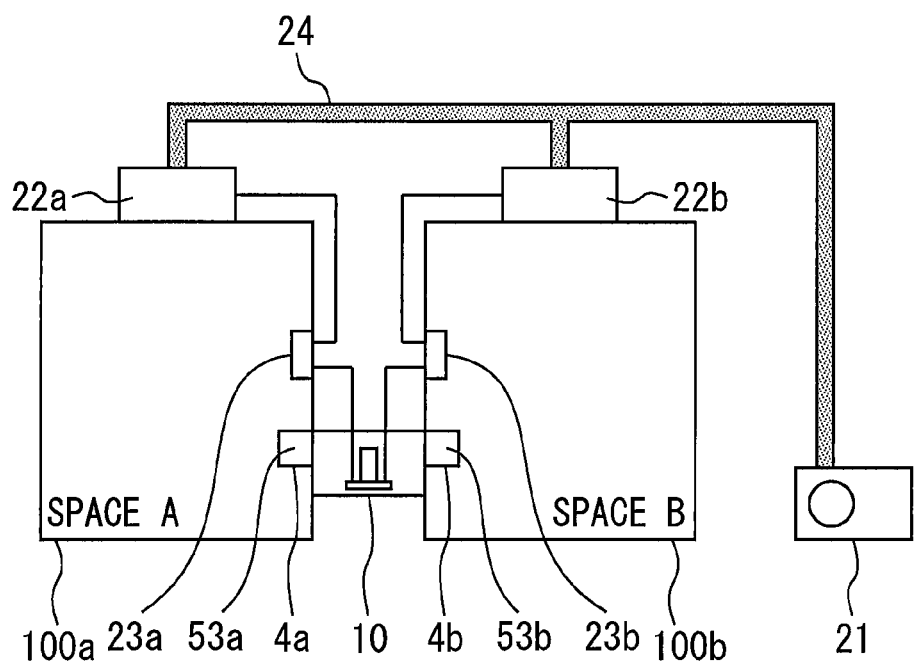
FIG. 5 is a view schematically showing an example of the installation of the refrigerant detection apparatus according to Embodiment 3 of the present invention.
Figure 6:
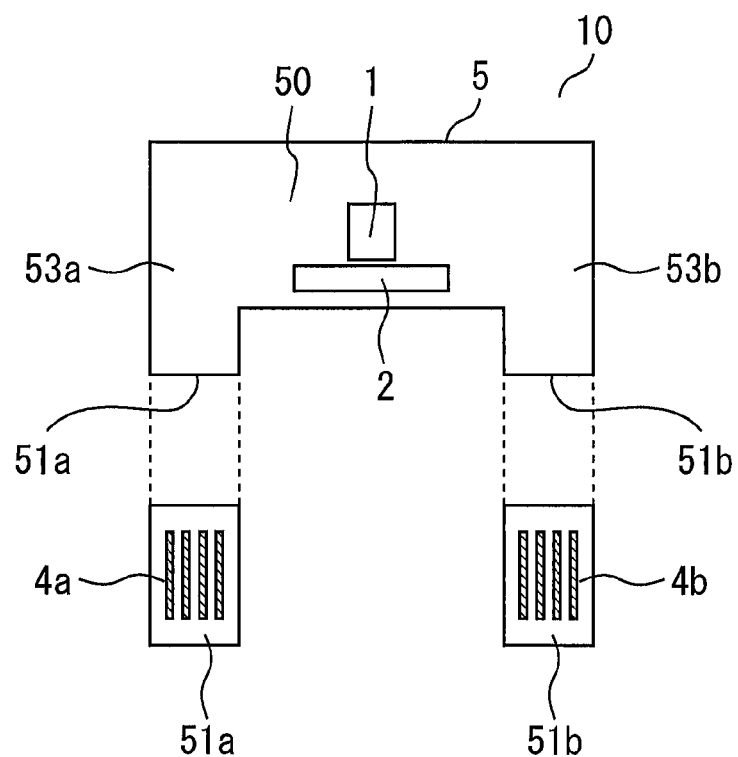
FIG. 6 is a view schematically showing another example of the configuration of the refrigerant detection apparatus according to Embodiment 3 of the present invention.

FIGS. 4 to 6 are associated with Embodiment 3 of the invention, FIG. 4 is a view schematically showing the configuration of the refrigerant detection apparatus, FIG. 5 is a view schematically showing an example of the installation of the refrigerant detection apparatus, and FIG. 6 is a view schematically showing another example of the configuration of the refrigerant detection apparatus.

In Embodiment 3 described herein, each of the first opening formation surface and the second opening formation surface of the casing is constituted by a surface that is directed downward in the configuration of Embodiment 1 or Embodiment 2 described above. Hereinafter, by using the case based on the configuration of Embodiment 1 as an example, a description will be given of the refrigerant detection apparatus according to Embodiment 3 with a focus on points different from Embodiment 1.

As shown in FIG. 4, in the refrigerant detection apparatus 10 according to Embodiment 3 of the invention, a first protrusion portion 53a is formed on one end side of the casing 5. A second protrusion portion 53b is formed on the other end side of the casing 5. The width of each of the first protrusion portion 53a and the second protrusion portion 53b in an up and down direction is smaller than the width of the sensor disposition portion 50 at the center of the casing 5 in the up and down direction.

A lower surface of the first protrusion portion 53a is the first opening formation surface 51a. A lower surface of the second protrusion portion 53b is the second opening formation surface 51b. Accordingly, the first opening formation surface 51a and the second opening formation surface 51b are directed vertically downward. Each of the first opening formation surface 51a and the second opening formation surface 51b is a flat surface. The first opening 4a formed in the first opening formation surface 51a is directed vertically downward. The second opening 4b formed in the second opening formation surface 51b is also directed vertically downward.

Next, a description will be given of an example in which the thus configured refrigerant detection apparatus 10 is installed such that the refrigerant detection apparatus 10 is usable with reference to FIG. 5. The refrigerant detection apparatus 10 according to Embodiment 3 is installed in a state in which the first protrusion portion 53a of the casing 5 protrudes toward the inside of the indoor space A from the wall surface of the first room 100a. In this state, the first opening 4a connects to the indoor space A of the first room 100a while being directed downward.

In addition, the refrigerant detection apparatus 10 is installed in a state in which the second protrusion portion 53b of the casing 5 protrudes toward the inside of the indoor space B from the wall surface of the second room 100b. In this state, the second opening 4b connects to the indoor space B of the second room 100b while being directed downward.

Note that other configurations are the same as those in Embodiment 1 or Embodiment 2, and the description thereof will be omitted.

When the refrigerant that is heavier than air leaks, the refrigerant that has leaked accumulates on the floor surface of the first room 100a or the second room 100b. When the leakage of the refrigerant continues, the position of the upper end of the area where the refrigerant has accumulated gradually rises. Subsequently, when the position of the upper end of the area where the refrigerant has accumulated reaches the first opening 4a or the second opening 4b, since the first opening 4a and the second opening 4b are directed downward, the refrigerant enters the casing 5 from the first opening 4a or the second opening 4b without any problem. Accordingly, also in the thus configured refrigerant detection apparatus 10, the effects similar to those of Embodiment 1 or Embodiment 2 can be exhibited.

Meanwhile, dust or the like that floats in the air in the indoor space A of the first room 100a and the indoor space B of the second room 100b slowly falls down from above. Accordingly, dust or the like is less likely to enter the casing 5 from the first opening 4a and the second opening 4b that are directed downward. Accordingly, in the thus configured refrigerant detection apparatus 10, contamination of the foreign object such as dust into the casing 5 can be prevented. In addition, the malfunction of the sensor 1 due to attachment of the foreign object such as dust to the sensor 1 can be prevented. Further, blockage of the first opening 4a and the second opening 4b with the foreign object such as dust deposited during long-term use or the like can be prevented.

Note that, as shown in FIG. 6, the sensor disposition portion 50 may be disposed above the first opening formation surface 51a and the second opening formation surface 51b. With this, even when the foreign object such as dust enters the casing 5 from the first opening 4a and the second opening 4b, entry of the foreign object such as dust having entered the casing 5 into the sensor 1 to be made hard.

Embodiment 4

Figure 7:
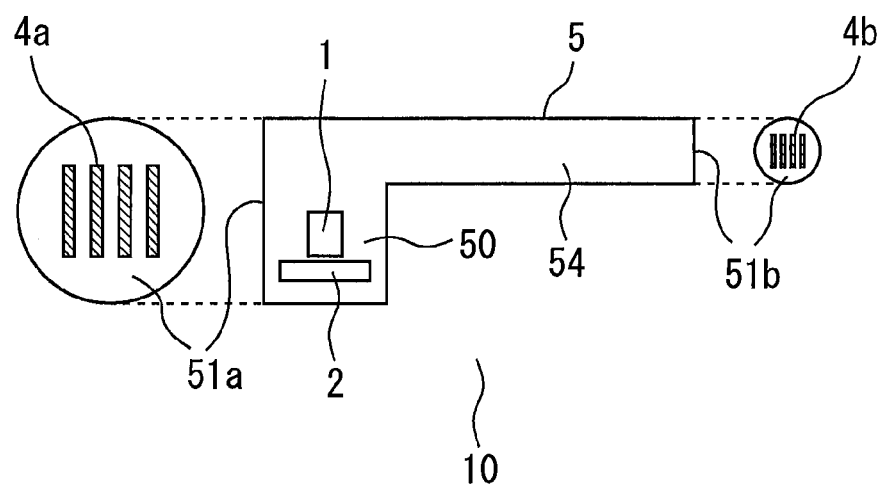
FIG. 7 is a view schematically showing the configuration of the refrigerant detection apparatus according to Embodiment 4 of the present invention.
Figure 8:
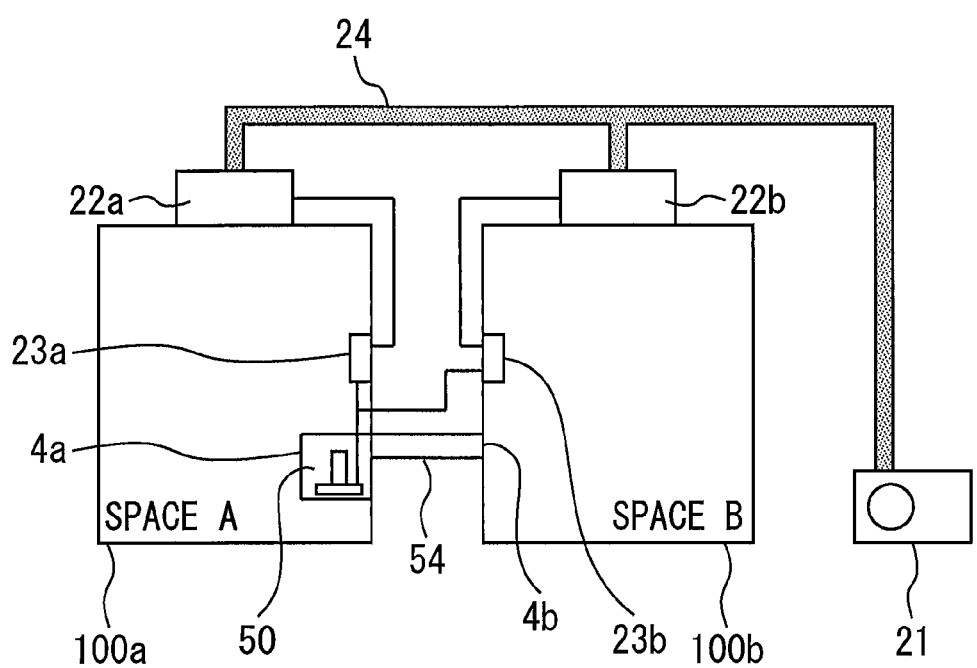
FIG. 8 is a view schematically showing an example of the installation of the refrigerant detection apparatus according to Embodiment 4 of the present invention.
Figure 9:
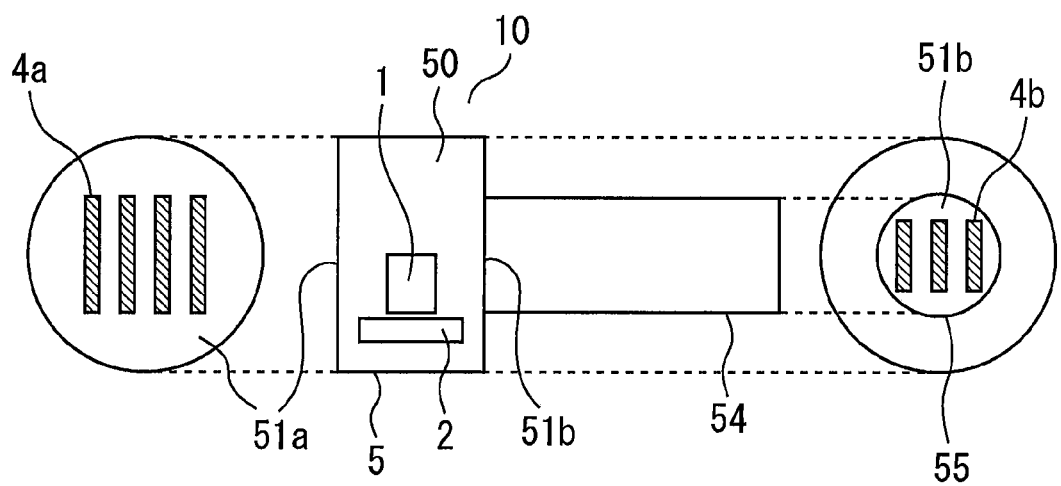
FIG. 9 is a view schematically showing another example of the configuration of the refrigerant detection apparatus according to Embodiment 4 of the present invention.
Figure 10:
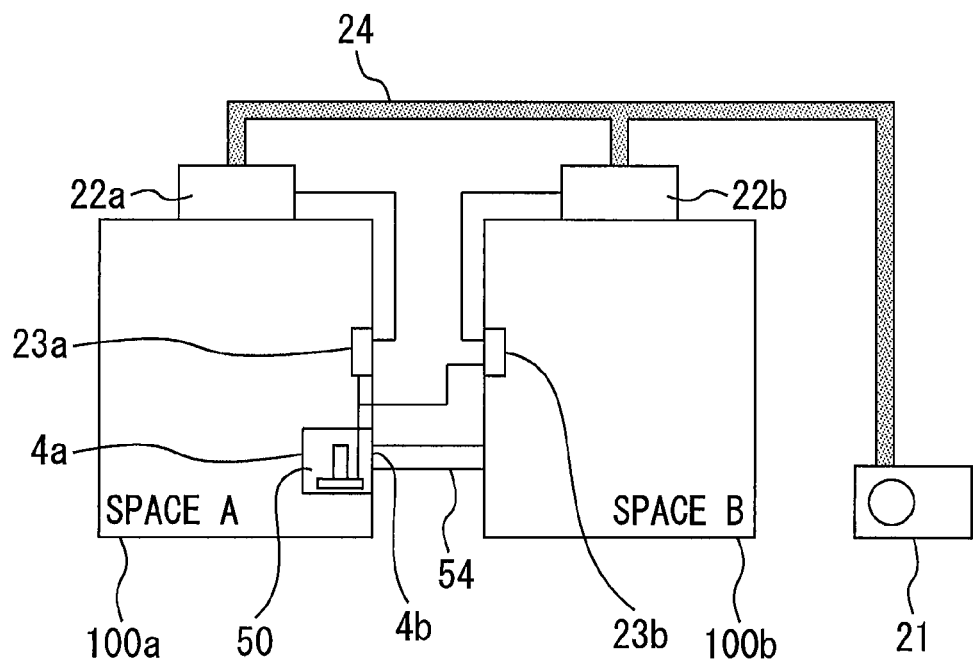
FIG. 10 is a view schematically showing another example of the installation of the refrigerant detection apparatus according to Embodiment 4 of the present invention.

FIGS. 7 to 10 are associated with Embodiment 4 of the invention, FIG. 7 is a view schematically showing the configuration of the refrigerant detection apparatus, FIG. 8 is a view schematically showing an example of the installation of the refrigerant detection apparatus, FIG. 9 is a view schematically showing another example of the configuration of the refrigerant detection apparatus, and FIG. 10 is a view schematically showing another example of the installation of the refrigerant detection apparatus.

In Embodiment 4 described herein, the sensor disposition portion of the casing is able to be disposed in a room that is able to be connected to the first opening, or in a room that is able to be connected to the second opening in the configuration of any one of Embodiments 1 to 3 described above. Hereinafter, by using the case based on the configuration of Embodiment 1 as an example, a description will be given of the refrigerant detection apparatus according to Embodiment 4 with a focus on points different from Embodiment 1.

As shown in FIG. 7, in the refrigerant detection apparatus 10 according to Embodiment 4 of the invention, the sensor disposition portion 50 is formed on one end side of the casing 5. In addition, an extension portion 54 is formed on the other end side of the casing 5. The extension portion 54 is provided to extend from the sensor disposition portion 50 to the other end side in a narrow way. That is, the extension portion 54 is narrower than the sensor disposition portion 50.

A side surface of the casing 5 on the side of the sensor disposition portion 50 is the first opening formation surface 51a. A tip surface of the extension portion 54, i.e., a side surface of the extension portion 54 on a side opposite to the side of the sensor disposition portion 50 is the second opening formation surface 51b. The first opening 4a is formed in the first opening formation surface 51a. The second opening 4b is formed in the second opening formation surface 51b. The internal space of the sensor disposition portion 50 communicates with the second opening 4b via the internal space of the extension portion 54.

Next, a description will be given of an example in which the thus configured refrigerant detection apparatus 10 is installed such that the refrigerant detection apparatus 10 is usable with reference to FIG. 8. In the refrigerant detection apparatus 10 according to Embodiment 4, the sensor disposition portion 50 of the casing 5 is disposed in one of the indoor space A of the first room 100a and the indoor space B of the second room 100b. FIG. 8 shows an example in which the sensor disposition portion 50 is disposed in the indoor space A of the first room 100a.

The extension portion 54 of the casing 5 passes through a wall between the first room 100a and the second room 100b from the side of the first room 100a in which the sensor disposition portion 50 is disposed to the side of the second room 100b. The second opening formation surface 51b formed at the tip of the extension portion 54 is exposed to the indoor space B of the second room 100b. Accordingly, the second opening 4b of the refrigerant detection apparatus 10 connects to the indoor space B of the second room 100b. In addition, the first opening formation surface 51a is exposed to the indoor space A of the first room 100a. Accordingly, the first opening 4a of the refrigerant detection apparatus 10 connects to the indoor space A of the first room 100a.

Accordingly, the air in the indoor space A of the first room 100a can enter the casing 5 through the first opening 4a, and reach the sensor disposition portion 50. In addition, the air in the indoor space B of the second room 100b can enter the casing 5 through the second opening 4b, and reach the sensor disposition portion 50 through the extension portion 54.

Note that other configurations are the same as those in any one of Embodiments 1 to 3, and the description thereof will be omitted.

Also in the thus configured refrigerant detection apparatus 10, the effects similar to those of any one of Embodiments 1 to 3 can be exhibited. Further, in Embodiment 4, the sensor disposition portion 50 is able to be disposed in a room that is able to be connected to the first opening 4a. Accordingly, it is not necessary to place the sensor disposition portion 50 in which the sensor 1 is housed in the wall between the first room 100a and the second room 100b. Accordingly, even in the case where the thickness of the wall between the first room 100a and the second room 100b is smaller than the thickness of the sensor disposition portion 50, the refrigerant detection apparatus 10 may be installed. In addition, the extension portion 54 that passes through the wall may be made to be thinner, thereby reducing the size of a hole formed in the wall.

Further, a maintenance worker or the like can easily access the sensor 1 and the leakage determination portion 2 from the first room 100a by enabling part of the sensor disposition portion 50 of the casing 5 to open and close, facilitating operations such as inspection, cleaning, and replacement of the sensor 1. In addition, the second opening formation surface 51b and the wall surface of the second room 100b can be flush with each other by causing the length of the extension portion 54 to match the thickness of the wall between the first room 100a and the second room 100b, and beauty particularly in the second room 100b is not spoiled.

Note that each of FIG. 7 and FIG. 8 shows an example in which the second opening formation surface 51b is provided at the tip portion of the extension portion 54. However, the position of the second opening formation surface 51b is not limited thereto, and the second opening formation surface 51b may also be provided, e.g., at some midpoint of the extension portion 54 or the like.

Next, a description will be given of another example of Embodiment 4 with reference to FIG. 9 and FIG. 10. As shown in FIG. 9, in another example, the sensor disposition portion 50 is formed on one end side of the casing 5. A side surface at one end of the sensor disposition portion 50 is the first opening formation surface 51a. A side surface at the other end of the sensor disposition portion 50 is the second opening formation surface 51b. In the second opening formation surface 51b, the extension portion 54 that protrudes to a side opposite to the side of the first opening formation surface 51a is formed. The extension portion 54 has, e.g., a hollow cylindrical shape. The extension portion 54 is narrower than the sensor disposition portion 50. One end of the extension portion 54 is connected to the second opening formation surface 51b. The other end, i.e., the tip of the extension portion 54 is open. In the following description, the other end (tip) of the extension portion 54 is also referred to as "an open end".

The first opening 4a is formed in the first opening formation surface 51a. The second opening 4b is formed in the second opening formation surface 51b. The second opening 4b is disposed inside the extension portion 54 in the second opening formation surface 51b. The internal space of the sensor disposition portion 50 communicates with the open end of the extension portion 54 via the second opening 4b and the internal space of the extension portion 54.

Next, a description will be given of an example in which the thus configured refrigerant detection apparatus 10 is installed such that the refrigerant detection apparatus 10 is usable with reference to FIG. 10. In the refrigerant detection apparatus 10 according to another example of Embodiment 4, the sensor disposition portion 50 of the casing 5 is disposed in one of the indoor space A of the first room 100a and the indoor space B of the second room 100b. FIG. 10 shows an example in which the sensor disposition portion 50 is disposed in the indoor space A of the first room 100a.

The extension portion 54 of the casing 5 passes through the wall between the first room 100a and the second room 100b from the side of the first room 100a in which the sensor disposition portion 50 is disposed to the side of the second room 100b. The open end of the extension portion 54 is exposed to the indoor space B of the second room 100b. Accordingly, the second opening 4b of the refrigerant detection apparatus 10 connects to the indoor space B of the second room 100b via the extension portion 54. In addition, the first opening formation surface 51a is exposed to the indoor space A of the first room 100a. Accordingly, the first opening 4a of the refrigerant detection apparatus 10 connects to the indoor space A of the first room 100a.

Accordingly, the air in the indoor space A of the first room 100a can enter the casing 5 through the first opening 4a, and reach the sensor disposition portion 50. In addition, the air in the indoor space B of the second room 100b can reach the second opening 4b through the extension portion 54. Subsequently, the air in the indoor space B of the second room 100b can enter the casing 5 through the second opening 4b, and reach the sensor disposition portion 50.

Also in the thus configured refrigerant detection apparatus 10, the effects similar to those of Embodiment 4 described above can be exhibited. A filter for removing the foreign object such as dust from passing air may be provided at the tip portion of the extension portion 54. With this configuration, contamination of the foreign object such as dust into the extension portion 54 can be prevented. Accordingly, a malfunction of the sensor 1 due to attachment of the foreign object such as dust to the sensor 1 can be prevented.

Note that the first room 100a and the second room 100b, and the first opening 4a and the second opening 4b in the above description are names that are used only for the sake of convenience. Accordingly, any of a plurality of rooms for which the refrigerant detection apparatus 10 is installed may be named the first room 100a or the second room 100b. Similarly, any of a plurality of openings of the casing 5 may be named the first opening 4a or the second opening 4b.

In addition, the number of rooms serving as detection targets of the refrigerant detection apparatus 10 is not limited to two. The refrigerant detection apparatus 10 may have the refrigerant having leaked in three or more rooms as the detection target. In this case, in the casing 5 of the refrigerant detection apparatus 10, at least openings equal in number to the rooms serving as the detection targets are formed. The individual openings are provided to be able to connect to different rooms.

INDUSTRIAL APPLICABILITY

The invention can be used as a refrigerant detection apparatus that has refrigerant having leaked in a plurality of rooms as a detection target. In particular, the invention can be used as a refrigeration cycle device that includes a cabinet that houses a refrigerant pipe in which refrigerant is filled, specifically, for example, a refrigerant detection apparatus that is used in combination with a floor-type, ceiling-type, or wall-type air conditioner.

REFERENCE SIGNS LIST

1 Sensor
2 Leakage determination portion
4a First opening
4b Second opening
5 Casing
10 Refrigerant detection apparatus
21 Outdoor unit
22a First indoor unit
22b Second indoor unit
23a First remote controller
23b Second remote controller
24 Refrigerant pipe
50 Sensor disposition portion
51a First opening formation surface
51b Second opening formation surface
52a First changeable portion
52b Second changeable portion
53a First protrusion portion
53b Second protrusion portion
54 Extension portion
100a First room
100b Second room

The invention claimed is:

1. A refrigerant detection apparatus comprising:
a sensor configured to detect refrigerant being filled in a refrigerant pipe of an air conditioner, and
a casing configured to house the sensor,
the casing having:
a first opening to connect to inside of a first room in which a first indoor unit of the air conditioner is installed, and
a second opening to connect to inside of a second room in which a second indoor unit of the air conditioner is installed, the second room being different from the first room,
the first opening being formed in a first opening formation surface of the casing,
the second opening being formed in a second opening formation surface of the casing,
the casing being disposed between a wall surface of the first room and a wall surface of the second room,
the first opening formation surface being exposed to the inside of the first room, and
the second opening formation surface being exposed to the inside of the second room.

2. The refrigerant detection apparatus according to claim 1,
wherein the casing includes a changeable portion configured to change one or both of relative positions and relative directions of the first opening formation surface and the second opening formation surface.

3. The refrigerant detection apparatus according to claim 1,
wherein the first opening formation surface and the second opening formation surface are directed downward.

4. The refrigerant detection apparatus according to claim 3,
wherein the casing includes a sensor disposition portion in which the sensor is disposed, and
wherein the sensor disposition portion is disposed above the first opening formation surface and the second opening formation surface.

5. The refrigerant detection apparatus according to claim 1,
wherein the casing includes a sensor disposition portion in which the sensor is disposed, and
wherein the sensor disposition portion is configured to be disposed in the first room.

6. The refrigerant detection apparatus according to claim 2,
wherein the casing includes a sensor disposition portion in which the sensor is disposed, and
wherein the sensor disposition portion is configured to be disposed in the first room.

7. The refrigerant detection apparatus according to claim 3,
wherein the casing includes a sensor disposition portion in which the sensor is disposed, and wherein the sensor disposition portion is configured to be disposed in the first room.

* * * * *